(12) United States Patent
Hon

(10) Patent No.: US 10,932,493 B2
(45) Date of Patent: Mar. 2, 2021

(54) ELECTRONIC CIGARETTE WITH COIL-LESS ATOMIZER

(71) Applicant: FONTEM HOLDINGS 1 B.V., Amsterdam (NL)

(72) Inventor: Lik Hon, Beijing (CN)

(73) Assignee: FONTEM HOLDINGS 1 B.V., Amsterdam (NL)

( * ) Notice: Subject to any disclaimer, the term of this patent is extended or adjusted under 35 U.S.C. 154(b) by 101 days.

(21) Appl. No.: 15/304,821

(22) PCT Filed: Apr. 23, 2014

(86) PCT No.: PCT/CN2014/076018
§ 371 (c)(1),
(2) Date: Oct. 17, 2016

(87) PCT Pub. No.: WO2015/161459
PCT Pub. Date: Oct. 29, 2015

(65) Prior Publication Data
US 2017/0042242 A1 Feb. 16, 2017

(51) Int. Cl.
*A24F 47/00* (2020.01)
*A61M 15/06* (2006.01)
*A61M 11/04* (2006.01)

(52) U.S. Cl.
CPC ......... *A24F 47/008* (2013.01); *A61M 11/042* (2014.02); *A61M 15/06* (2013.01);
(Continued)

(58) Field of Classification Search
None
See application file for complete search history.

(56) References Cited

U.S. PATENT DOCUMENTS 3,610,809 A * 10/1971 Eigenbrod ............... H01B 7/29
174/15.5
3,715,452 A * 2/1973 Long ..................... H01B 7/423
174/15.4
(Continued)

FOREIGN PATENT DOCUMENTS

CN 1040914 A 4/1990
CN 1045691 A 10/1990
(Continued)

OTHER PUBLICATIONS

C. N. Owston, "Electrical properties of Single carbon fibres", Jul. 1970, J. of Physics D: Applied Physics, 3, 1615.*
(Continued)

*Primary Examiner* — Ibrahime A Abraham
*Assistant Examiner* — Gyounghyun Bae
(74) *Attorney, Agent, or Firm* — Perkins Coie LLP; Kenneth H. Ohriner

(57) ABSTRACT

An electronic cigarette includes an atomizer having a coil-less heating element. The coil-less heating element may include a heating section and two leads electrically connected to the heating section. The heating section is made of one or more fiber materials. The two leads may be made of conductive materials that can conduct liquid to the heating section. Alternatively, the heating element may include one or more fiber materials with two conductive sections, and a heating section between the conductive sections. The heating section has a significantly higher electrical resistance than the conductive sections. The different electrical resistances may be achieved by modifying the fiber materials with a material (e.g. metals) having higher electronic conductivity. Different electrical resistances may also be achieved by modifying the shape of the fiber materials to
(Continued)

provide the conductive sections with a larger cross-section, and the heating section with a smaller cross-section.

21 Claims, 11 Drawing Sheets

(52) U.S. Cl.
CPC .............. *A61M 2205/0233* (2013.01); *A61M 2205/3653* (2013.01); *A61M 2205/8206* (2013.01)

(56) References Cited

U.S. PATENT DOCUMENTS

| | | | |
|---|---|---|---|
| 4,922,901 A * | 5/1990 | Brooks | A24F 47/006 128/202.27 |
| 4,947,874 A | 8/1990 | Brooks | |
| 9,277,770 B2 * | 3/2016 | DePiano | H05B 3/03 |
| 9,326,547 B2 | 5/2016 | Tucker et al. | |
| 9,423,152 B2 | 8/2016 | Ampolini | |
| 9,604,016 B2 * | 3/2017 | Price | A61M 15/009 |
| 9,993,023 B2 | 6/2018 | Tucker et al. | |
| 10,383,366 B2 | 8/2019 | Hon | |
| 10,398,176 B2 | 9/2019 | Hon et al. | |
| 10,537,135 B2 * | 1/2020 | Smith | A24F 40/80 |
| 2007/0207186 A1 | 9/2007 | Scanlon et al. | |
| 2008/0156326 A1 * | 7/2008 | Belcastro | A61M 15/0065 128/203.27 |
| 2009/0272379 A1 * | 11/2009 | Thorens | H05B 3/00 128/202.21 |
| 2011/0226236 A1 * | 9/2011 | Buchberger | A61M 15/0086 128/200.23 |
| 2012/0111347 A1 * | 5/2012 | Hon | A24F 47/008 131/329 |
| 2012/0285475 A1 * | 11/2012 | Liu | A24F 47/008 131/329 |
| 2013/0104916 A1 * | 5/2013 | Bellinger | A61M 11/041 131/328 |
| 2013/0192619 A1 * | 8/2013 | Tucker | H05B 3/12 131/329 |
| 2013/0213419 A1 | 8/2013 | Tucker et al. | |
| 2013/0255702 A1 | 10/2013 | Griffith, Jr. et al. | |
| 2014/0000638 A1 | 1/2014 | Sebastian et al. | |
| 2014/0007863 A1 | 1/2014 | Chen | |
| 2014/0123989 A1 * | 5/2014 | LaMothe | A24F 47/008 131/328 |
| 2014/0150783 A1 | 6/2014 | Liu | |
| 2014/0238422 A1 | 8/2014 | Plunkett et al. | |
| 2014/0238423 A1 | 8/2014 | Tucker et al. | |
| 2014/0238424 A1 * | 8/2014 | Macko | A24F 47/008 131/328 |
| 2014/0270727 A1 | 9/2014 | Ampolini et al. | |
| 2014/0270729 A1 * | 9/2014 | DePiano | A24F 47/008 392/397 |
| 2014/0334804 A1 | 11/2014 | Choi | |
| 2015/0090281 A1 * | 4/2015 | Chen | A24F 47/008 131/329 |
| 2015/0150306 A1 * | 6/2015 | Chen | A24F 47/008 131/329 |
| 2015/0196056 A1 * | 7/2015 | Liu | H05B 1/0244 131/328 |
| 2015/0257445 A1 * | 9/2015 | Henry, Jr. | A24F 47/008 131/328 |
| 2015/0296887 A1 * | 10/2015 | Zhu | A24F 47/008 131/329 |
| 2016/0010615 A1 | 1/2016 | Ishii | |
| 2018/0064169 A1 | 3/2018 | Biel et al. | |
| 2019/0037925 A1 | 2/2019 | Hon et al. | |
| 2019/0246699 A1 | 8/2019 | Qiu | |

FOREIGN PATENT DOCUMENTS

| | | |
|---|---|---|
| CN | 101843368 A | 9/2010 |
| CN | 102264420 A | 11/2011 |
| CN | 203168035 U | 9/2013 |
| CN | 103519351 A | 1/2014 |
| CN | 103556299 A | 2/2014 |
| CN | 203662017 U | 6/2014 |
| CN | 103948172 A | 7/2014 |
| EP | 0358002 A2 | 3/1990 |
| EP | 0358114 A2 | 3/1990 |
| TW | 201334713 A | 9/2013 |
| WO | 1998016088 A1 | 4/1998 |
| WO | 2013083631 A1 | 6/2013 |
| WO | 2013148810 A1 | 10/2013 |
| WO | 2014130772 A1 | 8/2014 |

OTHER PUBLICATIONS

International Searching Authority, "Written Opinion of the International Searching Authority" issued in International application No. PCT/CN2014/076018 (dated Jan. 15, 2015).
Great Britain Intellectual Property Office, Combined Search and Examination Report for GB1412906.8, dated Jan. 20, 2015, 7 pgs.
Great Britain Intellectual Property Office, Further Search Report for GB1412906.8, dated May 27, 2015, 2 pgs.
Great Britain Intellectual Property Office, Examination Report for GB1412906.8, dated Jun. 13, 2016, 3 pgs.
Taiwan Intellectual Property Office, Office Action and Search Report issued in Taiwan Patent Application No. 104113080 (dated Jul. 13, 2017).
EPO, "Extended European Search Report", for European Application No. 14889891.9, dated Nov. 8, 2017, 6 pgs.
Taiwan Intellectual Property Office, English Translation of First Office Action and Search Report for Taiwan Application No. 107114662; dated Sep. 10, 2018; 6 pages.
State Intellectual Property Office, First Office Action for Chinese Application No. 201480079630.0 with English Translation; dated Nov. 12, 2018; 9 pages.
State Intellectual Property Office, Second Office Action for Chinese Application No. 201480079630.0 with English translation; dated May 28, 2019; 8 pages.

* cited by examiner

PRIOR ART

Figure 5
(a)
(b)
(c)
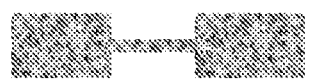
(d)
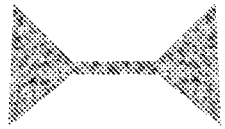

Figure 6
(a)
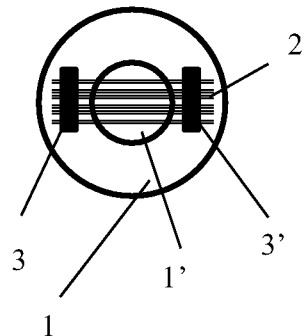
(b)
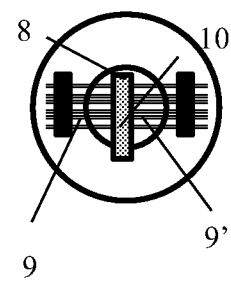
(c)
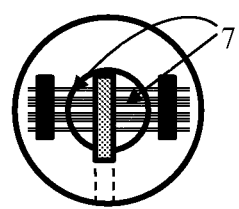
(d)
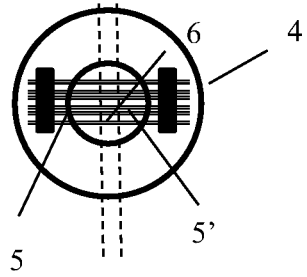

Figure 10
(a)
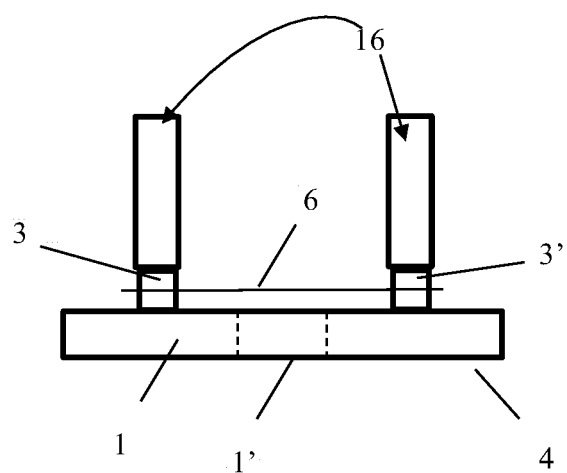
(b)
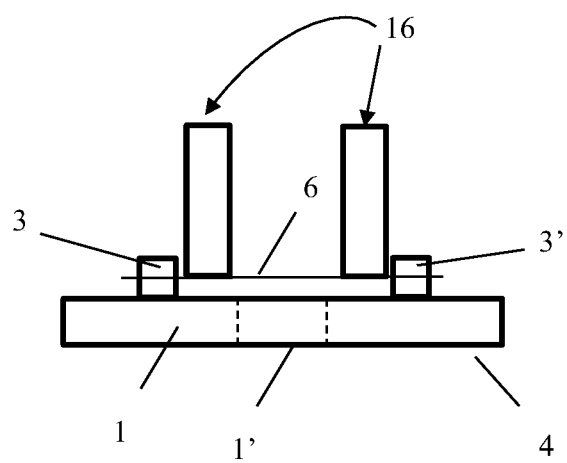
(c)
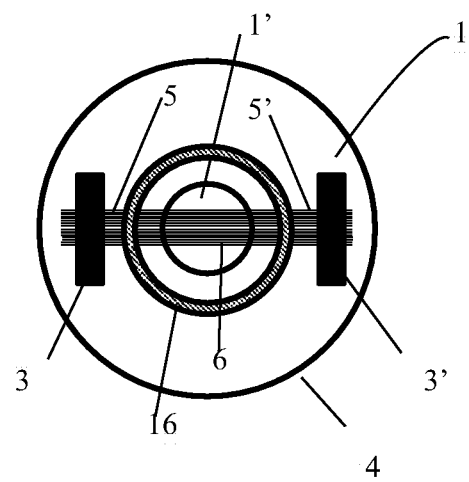

Figure 11
(a)
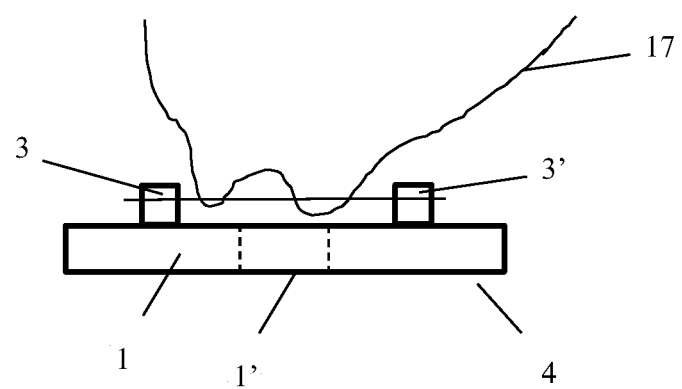
(b)
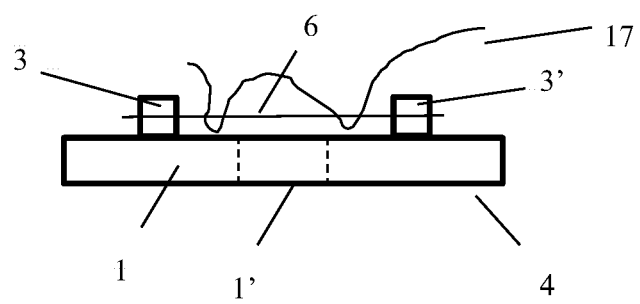

ELECTRONIC CIGARETTE WITH COIL-LESS ATOMIZER

FIELD OF THE INVENTION

The field of the invention is electronic cigarettes.

BACKGROUND OF THE INVENTION

Electronic cigarettes generally have an atomizer that vaporizes liquid with an electrically heated wire coil. Although heating coil atomizers have achieved significant success, they have several disadvantages. For example, a coil may not be a beneficial geometry for a heating element in certain designs. In addition, coils may be time consuming to assemble into the atomizer, especially smaller size coils. Engineering challenges accordingly remain in providing improved atomizers for electronic cigarettes.

BRIEF DESCRIPTION OF THE DRAWINGS

In the drawings, the same element number indicates the same element, in each of the views.

FIGS. 5a-5d illustrate a different shapes the fiber material felt 2 may adopt in a coil-less heating element.

FIGS. 6a-6d illustrate a method of coating conductive fibers to make the coil-less heating element shown in FIG. 2.

FIGS. 7a-7f illustrate a preparation process of the coil-less heating element shown in FIG. 4a.

FIG. 10(a) is an enlarged side view of the coil-less heating element of FIG. 2 in contact with a liquid supplying unit.

FIG. 10(b) is an enlarged side view of the coil-less heating element of FIG. 3 or 4 in contact with a liquid supplying unit.

FIG. 10(c) is a top cross-sectional view of the coil-less heating element of FIG. 3 in contact with a liquid supplying unit 16.

FIG. 11(a) is a side view of a wick winding around a coil-less heating element.

FIG. 11(b) is a side view of a wick winding around a coil-less heating element without contacting the heating section.

DETAILED DESCRIPTION

In one aspect, a coil-less atomizer has a heating element made of conductive fiber materials. A section of the conductive fibers may be coated with a conductive material to reduce the electrical resistance of the fibers. The conductive fiber material may be shaped to have areas of lesser and greater resistance. The coil-less atomizer need not have a separate wicking element to deliver liquid to the heating element. The coil-less atomizers disclosed can be miniaturized relative to conventional coil atomizers for electronic cigarettes, to provide more compact designs for electronic cigarettes. The reduced size of the atomizer may allow more space in the electronic cigarette for other components.

In another aspect, an electronic cigarette includes a coil-less atomizer having a heating element with a first lead, a second lead, and one or more conductive fibers electrically connected to the first and second leads. A section of the fibers forms a heating section. The conductive fibers may further comprise a first and a second conductive sections. The first and the second conductive sections are proximal to the first and second leads, respectively. The first and second conductive sections may have low electrical resistances (e.g., about 1Ω or less) relative to the electrical resistance of the heating section which has a higher electrical resistance (e.g., about 3Ω to about 5Ω, or about 1Ω to about 7Ω). The heating element may be designed to have a desired total electrical resistance of about 3Ω to about 6Ω, or about 1Ω to about 8Ω. When the e-cigarette is switched on, electricity flows between the electrodes through the conductive sections and the heating section. Electric current flowing through the heating element generates heat at the heating section, due to the higher resistance of the heating section.

Figure 1:
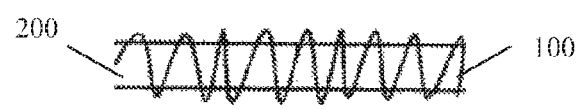
FIG. 1 illustrates a prior art atomizer having a coil heating element 100 and a wicking element 200.
Figure 2:
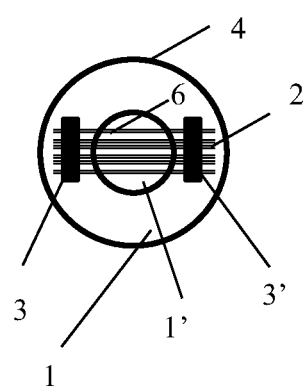
FIG. 2 is a top view of a coil-less heating element.

FIG. 2 shows a heating element 4 with the fibers 2 of the heating element mounted on a board 1 between two leads 3 and 3'. The board maybe a printed circuit board (PCB) with other electrical components, or it may be a board where the only electrical component is the heating element 4. The board may be an insulating material that provides sufficient support for the heating element, for example fiberglass. The fibers between the two leads 3 and 3' form the heating section 6. The board 1 may have a through hole 1' at least partially overlapping with part of the heating section 6 (e.g. overlapping with about 30% to about 100%, about 50% to about 100%, about 90% to about 100%, or about 100% of the heating section). The leads 3 and 3' may be made of any conductive materials. The leads may optionally also be made of conductive material that can transport liquid to the fibers 2. The fibers 2 may or may not extend laterally beyond the leads 3 and 3'. The fibers 2 may be positioned substantially parallel to each other between the leads 3 and 3', wherein the largest angle between a fiber and a line connecting the leads 3 and 3' is about 0 to about 10°, about 0 to about 5°, or about 0 to about 2°.

The conductive material used to make leads 3 and 3', which can transport liquid, may be porous electrode materials, including, conductive ceramics (e.g. conductive porous ceramics and conductive foamed ceramics), foamed metals (e.g. Au, Pt, Ag, Pd, Ni, Ti, Pb, Ba, W, Re, Os, Cu, Ir, Pt, Mo, Mu, W, Zn, Nb, Ta, Ru, Zr, Pd, Fe, Co, V, Rh, Cr, Li, Na, Tl, Sr, Mn, and any alloys thereof), porous conductive carbon materials (e.g. graphite, graphene and/or nanoporous carbon-based materials), stainless steel fiber felt, and any composites thereof. Conductive ceramics may comprise one or more components selected from the group consisting of oxides (e.g. $ZrO_2$, $TrO_2$, $SiO_2$, $Al_3O_2$, etc.), carbides (e.g. SiC, $B_4C$), nitrides (e.g. AlN), any of the metals listed above, carbon (e.g. graphite, graphene, and carbon-based materials), Si, and any combinations and/or composites of these materials. The term "composite" of two or more components means a material obtained from at least one processing of the two or more components, e.g. by sintering and/or depositing.

For clarity of illustration, FIG. 2 schematically shows only a few spaced apart fibers. However, the individual fibers shown may also be fibers in contact. The individual fibers may also be provided in the form of a fabric, where the fibers are in contact with each other to provide transport of liquid by capillary action. The diameters of the fibers may be about 40 μm to about 180 μm, or about 10 μm to about 200 μm. The fibers may have substantially similar or different diameters. The fibers may allow liquid to flow along or though the fibers by capillary action. The fiber materials may be organic fibers and/or inorganic fibers. Examples of inorganic fibers include carbon fibers, $SiO_2$ fibers, $TiO_2$ fibers, $ZrO_2$ fibers, $Al_2O_3$ fibers, $Li_4Ti_5O_{12}$ fibers, LiN fibers, Fe—Cr—Al fibers, NiCr fibers, ceramic fibers, conductive ceramic fibers, and modified fibers thereof. Examples of organic fibers include polymer fibers (e.g. polyaniline fibers, and aramid fibers), organometallic fibers and modifications of these types of fibers.

Fibers may be modified to improved surface properties (e.g. better hydrophilic properties to enhance wicking abilities) by exposure/coating/adhering the fibers to compounds having hydrophilic groups (e.g. hydroxide groups).

Fiber materials may also be modified to have desired electrical properties. For example the electrical conductivity of the fiber material may be changed by applying one or more modifying materials onto fiber material. The modifying materials may include $SnCl_2$, carbon (e.g. graphite, graphene and/or nanoporous carbon-based materials), any of the metals listed above, and/or alloys of them, to increase the electrical conductivity of the fibers, or the fiber material. Certain salts may be used as the modifying material to provide for lower conductivities. The modifying material may be applied to the fibers or fiber material by coating, adhering, sputtering, plating, or otherwise depositing the modifying material onto the fibers or fiber material.

In e-cigarette operation using the heating element shown in FIG. 2, liquid from a liquid storage component is provided onto the heating section through the leads. As the user inhales on the e-cigarette, vaporized liquid mixes with air flowing through the hole 1' which at least partially overlaps with part of the heating section 6 (e.g. overlapping with about 30% to about 100%, about 50% to about 100%, about 90% to about 100%, or about 100% of the heating section). In an alternative design, liquid may be provided directly onto the heating section via a wick or porous component, rather than through the leads.

Figure 3:
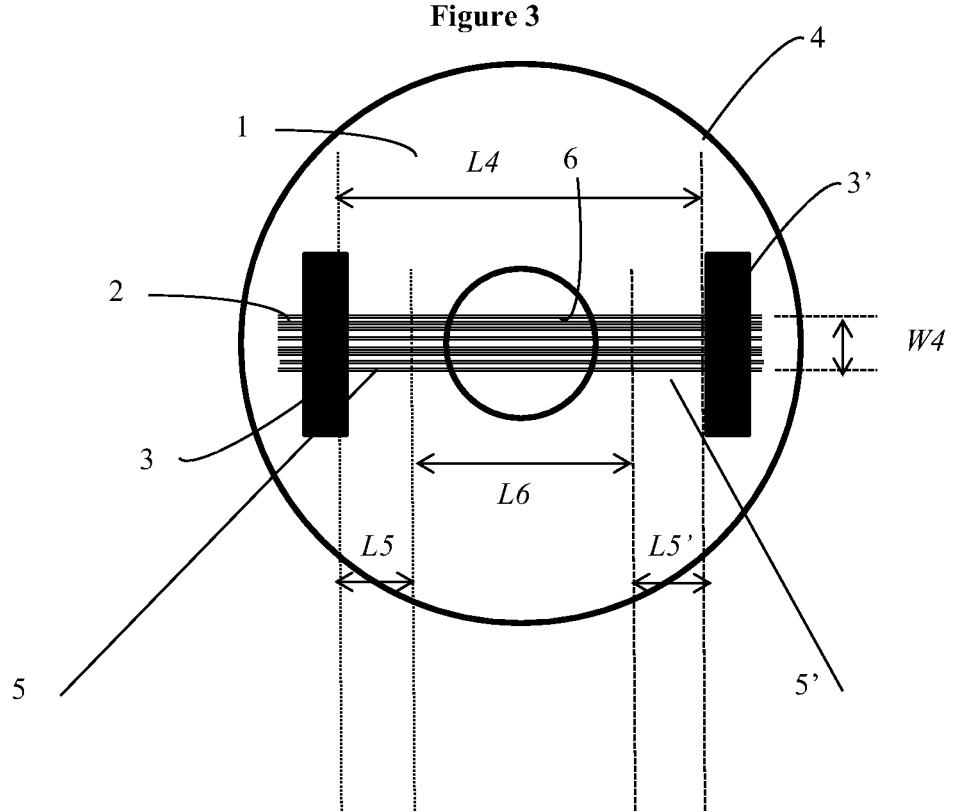
FIG. 3 is a top view of a coil-less heating element having coated conductive fibers.

FIG. 3 illustrates another heating element 4 where the fibers 2 are mounted on a board 1 between two leads 3 and 3'. The leads 3 and 3' may or may not be made of a conductive material capable of allowing liquid to reach the fiber materials 2, as described above relative to FIG. 2. The fibers may, or may not, extend laterally beyond the leads. The fibers between the leads 3, and 3' have a first conductive section 5 electrically connected to a first lead 3, a second conductive section 5' electrically connected to a second lead 3', and a heating section 6 between the first conductive section 5 and the second conductive section 5'. The conductive sections 5 and 5' have lower electrical resistance relative to the heating section 6. The heating section 6 and leads may have electrical resistances selected so that the total electrical resistance of the heating element 4 is suitable for the operation of an electric cigarette typically operating with DC battery voltage of from about 3 to 5 volts. In this case the heating element 4 may have a resistance of about 3~5Ω, or about 3.8Ω at room temperature.

Electrical resistance of a conductor can be calculated by the following formula:

$$R = \rho \frac{\ell}{A},$$

where R is electrical resistance (Ω), l is the length of the conductor, A is the cross-sectional area of the conductor ($m^2$), and ρ is the electrical resistivity of the material (Ω m).

The areas of the fibers in relation to the current may not be significantly different between the conductive sections 5 and 5' (A5, A5') and the heating section 6 (A6). However, the electrical resistance of the conductive sections should be lower than the heating section. This may be achieved by selectively modifying the fibers, as described above, to reduce to resistance of the conductive sections, and/or to increase the resistance of the heating section.

In FIG. 3, the conductive sections 5 and 5' have lengths of L5 and L6. The distance between the leads 3 and 3' is L4. Dimensions L4, L5, L5', L6, L4, A4, A5, A5', and A6 can be adjusted along with the selection of the one or more fibers, to achieve a specified electrical resistance. For example, for a heating element with an electrical resistance of about 3~5Ω, or about 3.8Ω, and L6 may be about 3 to about 4 mm. L4, L5, L5', L6, L4, A4, A5, A5', and A6 can also be selected according to the size of the electronic cigarette in which the atomizer is to be used. For example, the heating element 6 may be used in an electronic cigarette having a diameter of about 5 mm to about 10 mm.

Figure 4:
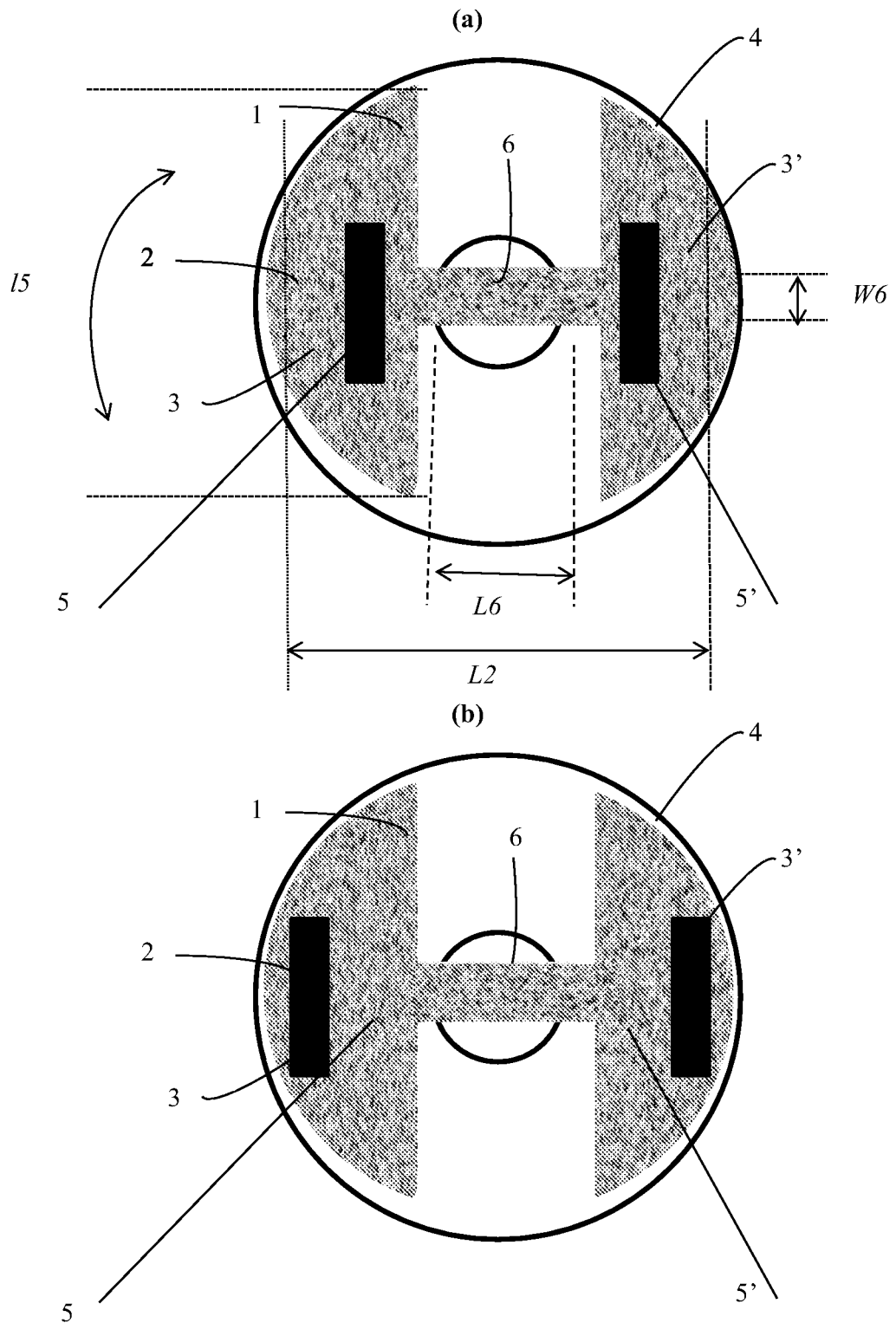
FIGS. 4a and 4b are top views of a coil-less heating element shaped to have different areas of electrical resistance.

In another embodiment, the different electrical resistances between the conductive and heating sections of the coil-less heating element are achieved by shaping the sections to have different cross-section with the current, as shown in FIG. 4.

FIG. 4a shows a coil-less heating element 4 having a pad of one or more fiber materials 2 electrically connected with two leads 3 and 3' on a board 1. The fiber material pad 2 has a first conductive sections 5 with an area of A5, a second conductive sections 5' with an area of A5', and a heating section 6 with an area of A6. The surfaces of the board 1 that contact the pad 2 may be conductive and electrically connected to the leads 3 and 3'. Alternatively, at least a significant portion (e.g. about 70% to about 99.9%, about 80% to about 99.9%, or about 90% to about 99.9%) of the surface of board 1 that contacts the conductive sections 5 and 5' of the pad 2 may be conductive and electrically connected to the leads 3 and 3'. Therefore, the areas of the conductive sections A5 and A5' may be considered as the cross-section area of the conductive section, and the area of the heating section A6 may be considered as the cross-section area of the heating section.

A5 and A5' are significantly larger than A6 (e.g. 3, 4, 5 or 10 to 20 times larger), so that the heating section 6 has higher electrical resistance than the conductive sections 5 and 5'. Although the thickness of the fiber material pad 2 may vary through the same pad, the depth differences have insignificant impact on the conductivities when compared to the area differences between the conductive sections 5 and 5' (A5, A5', respectively) and the heating section 6 (A6).

The fiber material pad 2 may adopt any shape having two wider parts linked by a narrow part. For example, the fiber material pad 2 may have a shape of a bow-tie or a dumb-bell (e.g., see. FIG. 5a). The wider end sections of the bow-tie or dumb-bell form the conductive sections. The narrow middle section of the bow-tie or dumb-bell form the heating section 6. In another example, the wider parts may be square (e.g., see. FIG. 5b), rectangle (e.g., see. FIG. 5c), triangle (e.g., see. FIG. 5d), or round shape (e.g., see. FIG. 5a). In certain embodiments, the fiber pad 2 may be a circular felt having a diameter of about 8 mm (L2), and a thickness of about 1 mm. The length of the heating section 6 (L6) may be about 3 to about 4 mm. The width of the heating section 6 (W6) may be about 1 mm. The arc length of the conductive section (l5) may be about 10 mm. The area of the conductive sections (A5 and A5') may be about 12 to about 20 mm², respectively. The area of the heating section (A6) may be about 3 to about 4 mm². The area ratio between the conductive section and the heating section is about (A5:A6) is about 3, 4, 5 or 10 to 20.

The diameters of the fibers of the pad may be about 40 µm to about 180 µm, or about 10 µm to about 200 µm, and the thickness of the fiber pad may be 0.5 to 2 mm or about 1 mm. The fiber materials and modifications described above may also be used on the pad of this embodiment.

Referring to FIGS. 4(a) and 4(b), the leads 3 and 3' may or may not be in contact with the fiber materials 2 at any position outside of the heating section, e.g. at the ends of the fiber materials 2. The conductive sections 5 and 5' may have an electric resistance of about 0 to about 1Ω; and the heating section 6 may have an electrical resistance of about 3Ω to about 5Ω such that the heating element has an electrical resistance of about 3Ω to about 6Ω.

FIGS. 6(a)-6(d) show a manufacturing process of the coil-less heating element shown in FIG. 2, which may include the following steps:

a) installing one or more fibers 2 on a board 1 between a first lead 3 and a second lead 3' (FIG. 6a). The board 1 has a through hole 1' between the first and second leads 3 and 3'.

b) covering a portion of the fibers between the first lead 3 and the second lead 3' with a mask 8 to provide a masked portion of the fibers 10 and unmasked portions of the fibers 9 and 9' (FIG. 6b). The through hole 1' at least partially overlaps with part of the masked portion of the fibers 10.

c) sputtering or otherwise applying at least part of the unmasked portions of the fibers 9 and 9' with a modifying agent 7 as described above, with the modifying agent 7 having a lower electrical resistance than the fibers before sputtering (FIG. 6c).

d) removing the mask 8 to provide a heating element as illustrated in FIG. 2.

FIGS. 7(a)-7(c) show a manufacturing process of the coil-less heating element shown in FIG. 4, which may include the following steps:

I) shaping a pad of one or more fiber materials 2 (FIG. 7a) to a shape having a first section 12, a second section 12', and a third section 11 (FIG. 7b) between the first and second sections 12 and 12' (FIG. 7b), wherein the first and second sections 12 and 12' have areas (A5, A5'), respectively larger than that of the third section 11 (A6, FIG. 7b); and II) installing the shaped pad 2 obtained from step I) on a board 1 between a first lead 3 and a second lead 3' (FIG. 7c). The narrow section 11 (FIG. 7b) becomes the heating section 6 (FIG. 7c); the first and second wider sections 12 and 12' (FIG. 7b) become the first and second conducting sections 5 and 5' (FIG. 7c), respectively.

FIGS. 7(d)-7(f) show optional processes that can be further carried out after Step (II), using the following steps:

III) covering a portion or all of the heating section 6 with a mask 8 to provide a masked portion of the fibers 10 and unmasked portions of the fibers 9 and 9' (FIG. 7d).

IV) applying at least part of the unmasked portions of the fibers 9 and 9' with a modifying agent 7 as described above, while leaving the masked portion of the fibers untreated, with the modifying agent 7 having a lower electrical resistance than the fibers before sputtering (FIG. 7e).

V) removing the mask 8 to provide a coil-less heating element.

The processes as discussed above may be adjusted to provide a heating element with an initial electrical resistance of about lower than desired. The heating element may then be further processed via sintering with the following steps to provide a final electrical resistance of ±0.1Ω of the desired electrical resistance (FIG. 8) via the following steps:

i) applying a known voltage (V) to the first lead 3 and the second lead 3', optionally the fiber 2 of the heating element 4 is coated or otherwise treated with a sintering material. As the heating element heats up, the resistance of the fiber 2 and/or the sintering material permanently changes.

ii) monitoring the current (I) through the electrical heating element 4.

iii) switching the voltage off when the measured current (I) reaches to a current corresponding to the desired electrical resistance of the heating element 4.

The sintering process may be applied in ambient air. Alternatively, the sintering process may be accelerated by adding oxygen to the process.

Figure 9:
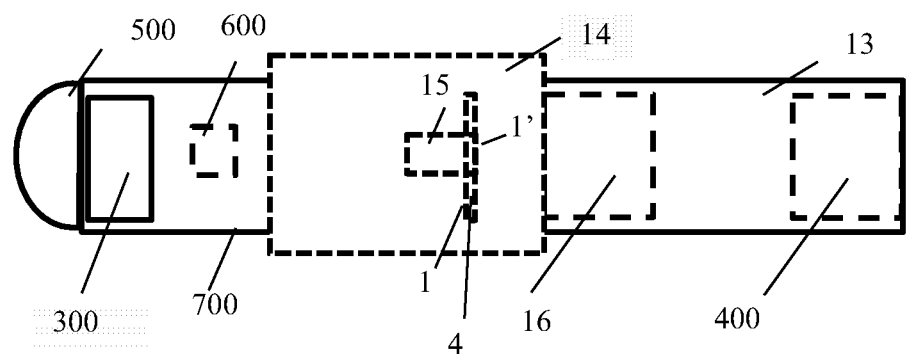
FIG. 9 shows an electronic cigarette having the coil-less heating element of FIG. 2, 3, or 4.

FIG. 9 shows an electronic cigarette 13 having a coil-less atomizer 14 and a liquid supply unit 16. The coil-less atomizer 14 includes a coil-less heating element 4 as illustrated in FIG. 2, 3, or 4, and an air flow passage 15 through at least part of the atomizer. The heating element 4 has a board 1 having a through hole 1'. The electronic cigarette 13 may further include a power source 300, such as battery or an electrical connector to a power source, a mouth piece 400, one or more LEDs 500 which light up in operation, and a sensor 600 within a housing 700.

In certain embodiments, the coil-less atomizer 14 may be wickless. The wickless and coil-less atomizer need not include a separate wicking element for conducting a liquid from the liquid supplying unit 16 to the coil-less heating element 4. Rather, liquid may flow directly from the liquid supplying unit to the fibers, fiber materials or the leads and then to the heating section of the fibers.

FIGS. 10(a)-10(c) illustrate several configurations for a coil-less heating element without a separate wicking element. FIG. 10a shows a side view of a wickless and coil-less atomizer 14. The coil-less heating element 4 has leads 3 and 3' that conduct liquid to the heating section 6. The materials of leads 3 and 3' can be conductive materials that can transport liquid, e.g. the porous electrode materials as set forth above, such as porous metals, foam nickel, porous conductive porcelain, stainless steel, and fiber felt. Said materials may be conductive electrodes and transport liquid. The liquid supplying unit 16 is in contact with the leads 3 and 3', which may conduct liquid through pores in the lead material, or via capillary action. No separate wicking element is needed. Although conductive sections are not required for the coil-less heating element 4 to function, the coil-less heating element 4 may include conductive sections as described above.

FIG. 10(b) shows a side view of another wickless and coil-less atomizer 14. The coil-less heating element 4 has conductive sections (e.g. the one shown in FIG. 3). The liquid supplying unit 16 is in contact with the coil-less heating element 4 on the conducting sections 5 and 5'. As the conducting sections 5 and 5' are capable of conducting liquid to the heating section 6, no wick is required. FIG. 10(c) shows a top view of such coil-less and wickless atomizer 14, wherein the liquid supplying unit 16 adopts a cylindrical shape. However, the liquid supplying unit 16 may have any shape capable of providing contact with one or both of the conducting sections 5 and 5' to supply the liquid flow. FIGS. 10(b) and 10(c) illustrate an embodiment wherein the coil-less heating element 4 has conductive sections as illustrated in FIG. 3. A coil-less heating element 4 without conductive sections may also be suitable for the configurations of FIGS. 10(b) and 10(c), if heating the part of the liquid supply unit 16 that contacts the heating element 4 is acceptable. The wickless configurations of FIGS. 10(*a*) and 10(*b*) may also be used with the coil-less heating element shown in FIGS. 4(*a*) and 4(*b*).

The coil-less atomizer 14 may also operate using a wick for moving liquid from a liquid source to the coil-less heating element. The wick can be any material that is capable of transporting liquid, such as ceramic fiber, quartz fiber, glass fiber, aramid fiber, common fiber, paper, cotton, porous ceramic, hemp, bamboo yarn, oxidized stainless steel mesh, wire mesh or braid and fabric or non-woven fabric materials. Optionally, zeolite particles may be further included in the wick to facilitate smooth vaporization.

FIG. 11(*a*) illustrates a side view of a coil-less atomizer using a wick. The coil-less heating element 4 may or may not have a conductive section, and its leads 3 and 3' may or may not be capable of transporting liquid to the heating section 6. The wick 17 may contact the coil-less heating element 4 at any part, e.g. the heating section 6, the lead 3 and 3' if applicable, and any combinations thereof. The wick may wind around the heating section and/or the leads 3 and/or 3', or adopt any suitable configuration.

For coil-less heating element 4 with conductive sections, the wick 17 may contact the coil-less heating element 4 at any part that can transport liquid to the heating section, e.g. the heating section 6, the conductive section 5, the conductive section 5', the leads 3 and 3' when applicable, and any combinations thereof, as shown in FIG. 11(*a*). Alternatively, the wick 17 may be configured to avoid the heating section 6, as shown in FIG. 11(*b*).

FIG. 11(*b*) shows a design where the coil-less heating element 4 has two conductive sections 5 and 5'. The wick may contact the coil-less heating element 4 at one or more parts except the heating section 6. Thus, the wick may contact the conductive section 5, the conductive section 5', the leads 3 and 3' when applicable, and any combinations thereof.

The heating elements described can be efficiently and conveniently produced in mass production, at low cost. They can also be manufactured with precise control of electrical resistance, leading to better performance when used in an electronic cigarette. The heating elements described may also be made in small sizes providing greater versatility for use in electronic cigarettes.

The coil-less atomizer described above may alternatively be described as an electrically conductive liquid wick having leads and a heating section. The heating section may be defined by an area of the wick having higher electrical resistance than the leads, so that electrical current passing through the wick heats the heating section to a high temperature, such as 100 to 350° C., while the leads, which are in contact with a bulk liquid source, remain relatively unheated. The wick, as a single element, heats liquid to generate vapor, and also conveys liquid from the bulk liquid source to the heating location. The electrically conductive liquid wick may be made of fibers, fabric, felt or porous matrix that can conduct both electrical current and liquid through the wick material, and with the electrical resistance of the wick non-uniform to provide a distinct heating section. The heating section and the leads may be integrally formed of the same underlying material, before treating the material to create different electrical resistances between the leads and the heating section. Generally the wick has a single heating section and two leads.

The wick may be flat, for example like fabric. The wick may be largely impermeable to air flow. The heating section of the wick may be oriented perpendicular to air flow within an electronic cigarette, with air flowing around the wick, rather than through the wick. Within the atomizing chamber or space, the wick may be perpendicular to the air flow and not loop back on itself, and also not extend longitudinally or parallel to the direction of air flow. In an electronic cigarette having dimensions comparable to a conventional tobacco cigarette (5-10 or 12 mm in diameter and 80-120 mm long), the bulk liquid source contains enough liquid for at least 100 puffs and up to 500 puffs (typically 0.1 to 2 mL).

Prophetic Example 1. A coil-less atomizer as shown in FIG. 3, prepared according to the process illustrated in FIGS. 6 and 8.

I) Installation and sputtering (FIG. 6)

A plurality of $SiO_2$ fibers 2 were installed to a circular PCB 1 between two metal leads 3 and 3'. The board had a through hole 1' between the two leads 3 and 3'. A mask 8 was placed to cover a portion (about 3 to about 4 mm lateral) of the fibers between the leads 3 and 3' to provide a masked portion of the fibers 10 and unmasked portions of the fibers 9 and 9'. The through hole 1' overlapped with the masked portion of the fibers 10. The unmasked portions of the fibers 9 and 9' were sputtered with Cr. The mask 8 was removed to provide a heating element 4 as illustrated in FIG. 2.

Figure 8:
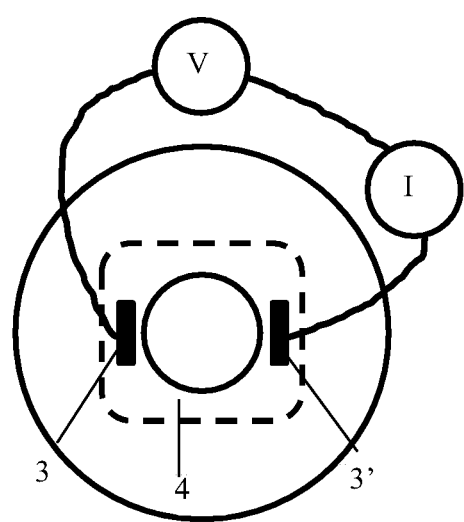
FIG. 8 illustrates a process of modifying the electrical resistance of a coil-less heating element to a desired range.

II) Sintering (FIG. 8)

The electrical resistance of the heating element 4 is about 2.8 to about 3.2Ω. A voltage of 3.8 V was applied to the leads 3 and 3', and the current (I) through the electrical heating element 4 was monitored. The voltage was switched off when the measured current (I) reached to 1 A, meaning that the electrical resistance of the heating element 4 was 3.8Ω.

The sintering process was applied in ambient air, and took about 1 minute.

The sintering process may be speeded up by adding oxygen air.

III) Coil-less atomizer without a wicking element (FIGS. 10*b* and 10*c*)

The coil-less heating element 4 with a desired resistance was prepared as described above. A liquid supply element may contact the conductive sections 5 and 5' and/or the heating section 6 of the heating element 4.

IV) Coil-less atomizer with a wicking element (FIGS. 11*a* and 11*b*)

Optionally, a wicking element 17 may be wound around the fibers of the heating element 4 to facilitate liquid flow from the liquid supply element to the heating element 4.

Prophetic Example 2. A coil-less atomizer as shown in FIG. 4, prepared according to the process illustrated in FIGS. 7 and 8.

Figure 7:
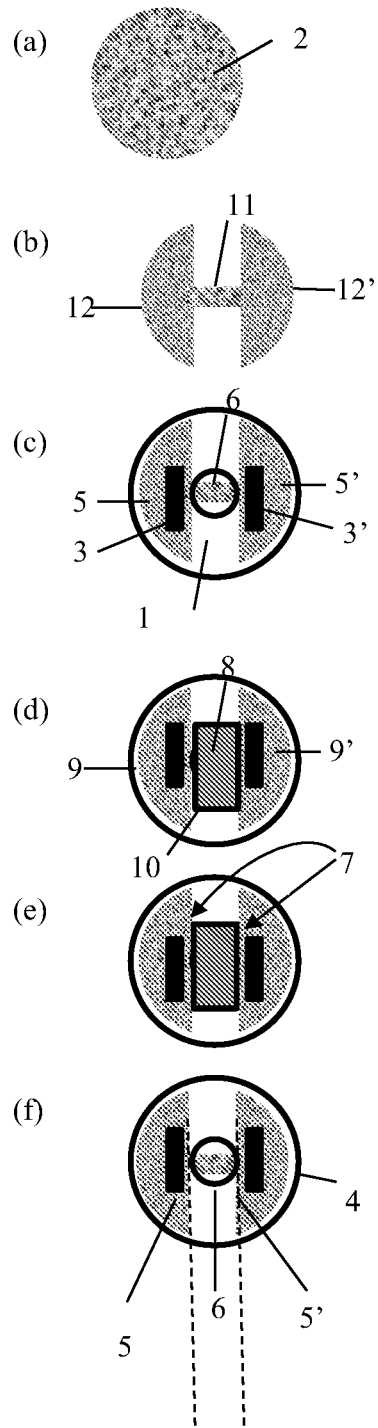

I) Installation and optional sputtering (FIG. 7)

A carbon fiber felt 2 is shaped by laser cutting or die punching process to provide a shape having two end sections and a middle section. The diameter of the carbon fiber felt 2 is about 8 mm. The thickness of the carbon fiber felt 2 is about 1 mm. The middle section has a length of about 3 to about 4 mm, and a width of about 1 mm. The end sections have an area of more than three or five times of the area of the middle section. The shaped carbon fiber felt 2 is installed on a circular PCB 1 between two metal leads 3 and 3'. The board 1 has a through hole 1' between the two leads 3 and 3'. The middle section of the carbon fiber felt 2 overlaps with the through hole 1'. The component obtained may be used as a heating element in a coil-less atomizer in an electronic cigarette.

A second sample heating element is further processed to lower the electrical resistance of the two end sections. As shown in FIG. 7, a mask 8 is placed over a portion of the middle section. The through hole 1' overlaps with the masked portion of the fibers 10. The unmasked portions of the fibers 9 and 9' are sputtered with $Cr^{++}$. The mask 8 is removed to provide a heating element 4 as illustrated in FIG. 3. II) Sintering (FIG. 8)

The electrical resistance of the heating element 4 is about 2.8 to about 3.2Ω. A voltage of 3.8 V is applied to the leads 3 and 3', and the current (I) through the electrical heating element 4 is monitored. The voltage is switched off when the measured current (I) reached 1 A, meaning that the electrical resistance of the heating element 4 was 3.8 Ω.

The sintering process is applied in ambient air, and may take about 1 minute.

III) Coil-less atomizer without a wicking element (FIGS. 10*b* and 10*c*)

The coil-less heating element 4 with a desired resistance is prepared as described above. A liquid supply element may contact the conductive sections 5 and 5' and/or the heating section 6 of the heating element 4.

IV) Coil-less atomizer with a wicking element (FIGS. 11*a* and 11*b*)

A wicking element 17 may be wound around the fibers of the heating element 4 to facilitate liquid flow from the liquid supply element to the heating element 4.

As used herein, "about" when used in front of a number means ±10% of that number. Reference to fibers includes fiber material (woven or non-woven). Reference to liquid here means liquids used in electronic cigarettes, generally a solution of propylene glycol, vegetable glycerin, and/or polyethylene glycol 400 mixed with concentrated flavors and/or nicotine, and equivalents. References here to fiber materials and capillary action include porous materials, where liquid moves internally through a solid porous matrix. Each of the elements in any of the embodiments described may of course also be used in combination with any other embodiment. Reference to electronic cigarette includes electronic cigars and pipes, as well as components of them, such as cartomizers.

The examples and embodiments described herein are intended to illustrate various embodiments of the invention. As such, the specific embodiments discussed are not to be construed as limitations on the scope of the invention. It will be apparent to one skilled in the art that various equivalents, changes, and modifications may be made without departing from the scope of invention, and it is understood that such equivalent embodiments are to be included herein.

The invention claimed is:

1. An electronic cigarette having a battery, and a liquid supply unit, comprising:
    an atomizer having a heating element including a first conductive section, a second conductive section, and a heating section between the first conductive section and the second conductive sections, with the heating section and the first conductive section comprising fibers, the first and second conductive sections electrically connected to the battery for conducting electrical current from the battery through the heating section, at least the first conductive section contacted by liquid from the liquid supply unit, and at least first conductive section moving the liquid to the heating section;
    with the heating element treated so that the heating section has an electrical resistance 3 to 7 times higher than the first conductive section or the second conductive section; and
    an air flow passage through the atomizer, with the heating section oriented perpendicular to the air flow passage.

2. The electronic cigarette of claim 1 wherein the conductive sections are integrally formed with the heating section from a single piece of material.

3. The electronic cigarette of claim 1 wherein both conductive sections are in direct or indirect contact with liquid in the liquid supply unit.

4. The electronic cigarette of claim 1 wherein the heating section is impermeable to air flow, with air in the air flow passage flowing around the sides of the heating section.

5. The electronic cigarette of claim 1 wherein the first conductive section has a cross section area greater than the heating section.

6. An electronic cigarette, comprising:
    a battery;
    a liquid supply unit;
    an atomizer having a heating element including a first conductive section, a second conductive section, and a heating section, the heating section and the first conductive section comprising fibers;
    the first and second conductive sections electrically connected to the battery, and with the first conductive section contacted by liquid from the liquid supply unit; and
    the heating section having an electrical resistance higher than the first and second conductive sections, the heating section impermeable to air flow, and the first and second conductive sections and the heating section having different cross-section areas.

7. The electronic cigarette of claim 6 with the second conductive section comprising fibers and with the second conductive section in contact with liquid from the liquid supply unit.

8. The electronic cigarette of claim 6 further including a wick contacting the heating element and the liquid supply unit.

9. The electronic cigarette of claim 6 wherein the heating element has a total electrical resistance of 1 to 8 ohms, and each of the first conductive section and the second conductive section has an electrical resistance of 1 ohm or less.

10. The electronic cigarette of claim 6 wherein the liquid from the liquid supply unit flows continuously via capillary action through at least the first conductive section to the heating section, as the liquid is vaporized at the heating section.

11. The electronic cigarette of claim 6 further including an air flow passage through the atomizer, with the heating section oriented perpendicular to the air flow passage.

12. The electronic cigarette of claim 6 wherein the heating section has an electrical resistance 3 to 7 times higher than the second conductive section.

13. The electronic cigarette of claim 6 wherein the first conductive section has an electrical resistance of 1 ohm or less and wherein the heating section has an electrical resistance of 3 to 8 ohms.

14. The electronic cigarette of claim 6 wherein the heating element has a total electrical resistance of 1 to 8 ohms.

15. An electronic cigarette, comprising:
    a battery;
    a liquid supply unit;
    an atomizer having a heating element comprising a fiber pad including a heating section between a first conductive section and a second conductive section;
    an air flow passage through the atomizer, with the heating section oriented perpendicular to the air flow passage;
    the first and second conductive sections electrically connected to the battery, and the first conductive section provided with liquid from the liquid supply unit;
    the heating section having an electrical resistance higher than the first and second conductive sections; and wherein the heating section is impermeable to air flow, with air in the air flow passage flowing around the sides of the heating section.

16. The electronic cigarette of claim 15 wherein the first conductive section has an electrical resistance of 1 ohm or less and wherein the heating section has an electrical resistance of 3 to 8 ohms.

17. The electronic cigarette of claim 15 wherein the heating element has a total electrical resistance of 1 to 8 ohms.

18. The electronic cigarette of claim 15 wherein the heating section has an electrical resistance 3 to 7 times higher than the second conductive section.

19. The electronic cigarette of claim 15 wherein the first conductive section has an electrical resistance of about 1 ohm or less and wherein the heating section has an electrical resistance of about 3 to 8 ohms.

20. The electronic cigarette of claim 15 wherein the heating section has a total electrical resistance of 1 to 8 ohms.

21. The electronic cigarette of claim 15 wherein the first conductive section has a cross section area greater than the heating section.

* * * * *